United States Patent
Hosaka et al.

(10) Patent No.: US 7,303,792 B2
(45) Date of Patent: Dec. 4, 2007

(54) DIAMINOBENZENE DERIVATIVE, POLYIMIDE PRECURSOR AND POLYIMIDE OBTAINED THEREFROM, AND ALIGNING AGENT FOR LIQUID CRYSTAL

(75) Inventors: Kazuyoshi Hosaka, Chiba (JP); Hirotsugu Taki, Chiba (JP); Hideyuki Nawata, Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 60 days.

(21) Appl. No.: 10/538,060

(22) PCT Filed: Dec. 10, 2003

(86) PCT No.: PCT/JP03/15800

§ 371 (c)(1),
(2), (4) Date: Jun. 9, 2005

(87) PCT Pub. No.: WO2004/052962

PCT Pub. Date: Jun. 24, 2004

(65) Prior Publication Data

US 2006/0246230 A1    Nov. 2, 2006

(30) Foreign Application Priority Data

Dec. 11, 2002    (JP) .................... 2002-359224

(51) Int. Cl.
*C09K 19/00*    (2006.01)
(52) U.S. Cl. .................. 428/1.3; 428/1.25; 428/1.26; 528/324; 558/418; 564/347
(58) Field of Classification Search ................ 564/305, 564/347; 428/1.3, 1.25, 1.26; 528/324; 558/418
See application file for complete search history.

(56) References Cited

U.S. PATENT DOCUMENTS

| | | | |
|---|---|---|---|
| 5,521,160 A * | 5/1996 | Chucholowski et al. ...... 514/42 |
| 6,656,971 B2 * | 12/2003 | Wu et al. .................... 514/599 |
| 2002/0165275 A1 * | 11/2002 | Wu et al. .................... 514/518 |

FOREIGN PATENT DOCUMENTS

| | | |
|---|---|---|
| EP | 0 663 391 | 7/1995 |
| JP | 2-282726 | 11/1990 |
| JP | 3-179323 | 8/1991 |
| JP | 5-27244 | 2/1993 |
| JP | 9-278724 | 10/1997 |
| WO | 97/30107 | 8/1997 |
| WO | WO 9838168 | * 9/1998 |

* cited by examiner

*Primary Examiner*—Yvonne (Bonnie) Eyler
*Assistant Examiner*—Chukwuma Nwaonicha
(74) *Attorney, Agent, or Firm*—Oblon, Spivak, McClelland, Maier & Neustadt, P.C.

(57) ABSTRACT

The present invention provides a novel diamine which is especially useful as a material for a resin for a liquid crystal alignment film, a polyimide precursor and a polyimide synthesized by using the diamine, and a treating agent for liquid crystal alignment containing such a polymer, which gives a liquid crystal alignment film having a high pretilt angle of liquid crystal, excellent thermal stability of the pretilt angle and small dependence of the pretilt angle on rubbing pressure.

A diaminobenzene derivative represented by the formula (1):

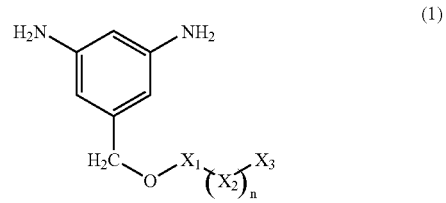

wherein $X_1$ and $X_2$ are cyclic groups, and $X_3$ is selected from an alkyl group, an alkoxy group, a fluoroalkyl group, a fluoroalkoxy group, a fluorine atom, a chlorine atom, a bromine atom and a cyano group; a polyimide precursor and a polyimide synthesized by using the diaminobenzene derivative as a part of the material; and a treating agent for liquid crystal alignment containing at least one of the polymers.

20 Claims, No Drawings

DIAMINOBENZENE DERIVATIVE, POLYIMIDE PRECURSOR AND POLYIMIDE OBTAINED THEREFROM, AND ALIGNING AGENT FOR LIQUID CRYSTAL

TECHNICAL FIELD

The present invention relates to a novel diaminobenzene derivative, a polyimide precursor and a polyimide synthesized by using the compound as a part of the material, and a treating agent for liquid crystal alignment containing such a polymer.

BACKGROUND ART

Heretofore, a polyimide has been widely used as a protective material, an insulating material or a liquid crystal alignment film for a liquid crystal display device in the electric or electronic field by virtue of its characteristics such as high mechanical strength, heat resistance and solvent resistance. Especially in an application to the liquid crystal alignment film, a polyimide or a polyamic acid as a polyimide precursor has mostly been employed because of the uniformity and durability of the coating film surface. However, in recent years, developments in the electric and electronic fields have been remarkable, and higher properties have been correspondingly required for the material to be employed. Also for a polyimide, it has been required to impart new properties which conventional polyimides do not have.

When new properties are to be imparted to the polyimide, it is simple and effective to employ a method of introducing a new structure into a tetracarboxylic acid derivative or a diamine as a material for the polyimide and using it in combination with various materials. Especially, with the diamine as compared with the tetracarboxylic acid derivative, a compound having the desired structure introduced can easily be synthesized. Therefore, for the purpose of imparting new properties, it has been common to use a diamine having a specific structure as the material for the polyimide.

Whereas, one of the properties required for a liquid crystal alignment film is to impart a high pretilt angle to liquid crystal. In this respect, it is known that a high pretilt angle can be obtained by a polyimide liquid crystal alignment film using, as a material, a diamine having a long chain alkyl group or a fluoroalkyl group as a side chain (see, for example, JP-A-2-282726). Further, it is known that a high pretilt angle is likewise obtainable also when a diamine having an aromatic group, an aliphatic ring group or a heterocyclic ring group as a side chain is used as a material (see, for example, JP-A-3-179323).

However, along with the progress in high densification and high performance of liquid crystal displays, the stability of the pretilt angle in a process for producing a liquid crystal display device and the stability of the pretilt angle in an environment for use of the liquid crystal display device become increasingly important in addition to obtaining the high pretilt angle. For example, there was a case such that the pretilt angle decreases when a liquid crystal display device is heated at a temperature higher than the isotropic temperature of liquid crystal (hereinafter referred to as isotropic treatment). Especially, the decrease in the pretilt angle becomes particularly remarkable in a case where the pretilt angle is high or in a case where the curing temperature at the time of forming the liquid crystal alignment film, is low. Further, in a case where the curing temperature is high at the time of forming the liquid crystal alignment film, there has been a problem such that the pretilt angle can hardly be made high or tends to fluctuate. So as to solve such problems, the applicants of the present invention have already reported a polyimide liquid crystal alignment film using, as a material, a diamine having in its side chain moiety a structure comprising a cyclic substituent selected from aromatic rings, aliphatic rings and heterocyclic rings, an aliphatic ring and a long chain alkyl group (see JP-A-9-278724).

Further, as a question relating to the pretilt angle of liquid crystal, the stability of the pretilt angle in rubbing treatment may be mentioned. Especially, there will be a problem in a stable production of liquid crystal display devices if the dependence of the degree of the pretilt angle on rubbing pressure is high. However, a diamine for increasing the pretilt angle, which has been proposed heretofore, tends to be insufficient in properties by itself, and therefore it was required to suitably select a material for a polyimide to be used together with the diamine. Namely, it has been desired to produce a diamine for increasing a pretilt angle, which has not only thermal stability of the pretilt angle but also stability under the conditions of rubbing treatment.

DISCLOSURE OF THE INVENTION

The present invention has been made under the above circumstances, and the object is to provide a novel diamine which is especially useful as a material for a resin for a liquid crystal alignment film, more particularly, a novel diamine as a material for a liquid crystal alignment film having a high effect of increasing the pretilt angle, excellent thermal stability of the pretilt angle, and small dependence of the pretilt angle on rubbing pressure; a polyimide precursor or a polyimide synthesized by using this diamine as a part of the material; and a treating agent for liquid crystal alignment containing such a polymer, which gives a liquid crystal alignment film having a high pretilt angle of liquid crystal, excellent thermal stability of the pretilt angle and small dependence of the pretilt angle on rubbing pressure.

As a result of an extensive study on the above-mentioned object, the present inventors have found a diaminobenzene derivative having a specific structure.

Namely, the above object has been accomplished by a diaminobenzene derivative represented by the formula (1):

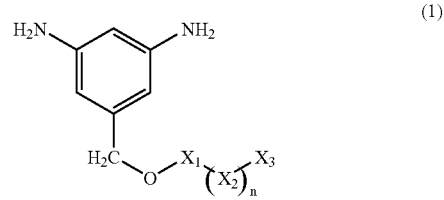

wherein $X_1$ and $X_2$ are each independently a cyclic group selected from a benzene ring, a cyclohexane ring and a heterocyclic ring, optional hydrogen atom(s) on the cyclic group may be substituted by substituent(s) selected from a $C_{1-3}$ alkyl group, a $C_{1-3}$ alkoxy group, a $C_{1-3}$ fluoroalkyl group, a $C_{1-3}$ fluoroalkoxy group, a fluorine atom, a chlorine atom, a bromine atom and a cyano group, n is an integer of 0 or 1, and $X_3$ is a member selected from a $C_{1-32}$ alkyl group, a $C_{1-32}$ alkoxy group, a $C_{1-32}$ fluoroalkyl group, a $C_{1-32}$ fluoroalkoxy group, a fluorine atom, a chlorine atom, a bromine atom and a cyano group; a polyimide precursor or a polyimide synthesized by using the diaminobenzene derivative represented by the formula (1), as a part of the material; and a treating agent for liquid crystal alignment containing at least one of the polyimide precursor and the polyimide synthesized by using the diaminobenzene derivative represented by the formula (1), as a part of the material.

BEST MODE FOR CARRYING OUT THE INVENTION

Now, the present invention will be described in detail.

The diaminobenzene derivative of the present invention is one having the structure represented by the formula (1) and can be used as a material for various polymers, just like a usual primary diamine. It is a novel diamine which is useful especially when it is used as a material for a resin for a liquid crystal alignment film.

The diaminobenzene derivative of the present invention represented by the formula (1) consists of a 3,5-diaminobenzyl ether moiety (1a) as a main skelton and —$X_1$—$(X_2)_n$—$X_3$ as a side chain.

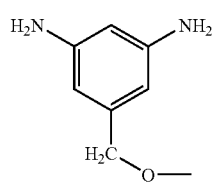

The above (1a) is a diaminobenzene skeleton, and therefore the side chain density can be increased when formed into a polymer. Further, the (1a) has a methylene ether bond (—$CH_2O$—) as a bonding group to the side chain, while it has amino groups at 3,5-positions, and therefore, it has an effect of increasing polymerization reactivity of the amino groups. Further, the bonding position of the side chain is distanced from the amino groups, whereby the side chain will be distanced from the polymer main chain when polymerized, and therefore, the liquid crystal alignment film will have a high effect of increasing the pretilt angle. On the other hand, the side chain has a ring structure, and therefore it has an effect of increasing the thermal stability of the side chain. It is most important for the diaminobenzene derivative of the present invention to employ the methylene ether bond (—$CH_2O$—) as a bond between the benzene ring as a part of the main chain and the cyclic group of the side chain in the polymer. The polymer having such a diaminobenzyl cyclic group ether structure can have the stability to the rubbing pressure in addition to the thermal stability of the pretilt angle, when used as a liquid crystal alignment film.

In the formula (1), $X_1$ and $X_2$ are each independently a cyclic group selected from a benzene ring, a cyclohexane ring and a heterocyclic ring. The heterocyclic ring may, for example, be a pyrrole ring, a furan ring, a thiophene ring, an imidazole ring, an oxazole ring, a thiazole ring, a pyrazole ring, a pyrroline ring, a pyrrolidine ring, a pyridine ring or a pyrimidine ring. Optional hydrogen atom(s) on such a cyclic group may be substituted by substituent(s) selected from a $C_{1-3}$ alkyl group, a $C_{1-3}$ alkoxy group, a $C_{1-3}$ fluoroalkyl group, a $C_{1-3}$ fluoroalkoxy group, a fluorine atom, a chlorine atom, a bromine atom and a cyano group. However, from the viewpoint of availability of the material and efficiency in the synthetic reaction, such hydrogen atom(s) may most preferably be not substituted, and preferably be substituted by a methyl group, a methoxy group, a trifluoromethyl group, a trifluoromethoxy group, a fluorine atom, a chlorine atom, a bromine atom or a cyano group.

Among such cyclic groups, a benzene ring or a cyclohexane ring is preferred from the viewpoint of availability of the material, efficiency in the synthetic reaction and the liquid crystal alignment property in the application to a liquid crystal alignment film. Further, such a benzene ring or a cyclohexane ring is preferably bonded at 1,4-positions of the six-membered ring.

In the formula (1), n is 0 or 1, and is preferably 1 for the effect of increasing the pretilt angle and the thermal stability of the pretilt angle in the application to the liquid crystal alignment film. If after-mentioned $X_3$ is a $C_{1-32}$ fluoroalkyl group or a $C_{1-32}$ fluoroalkoxy group, n may be 0, because such $X_3$ will supplement the above effect.

In the formula (1), $X_3$ is a member selected from a $C_{1-32}$ alkyl group, a $C_{1-32}$ alkoxy group, a $C_{1-32}$ fluoroalkyl group, a $C_{1-32}$ fluoroalkoxy group, a fluorine atom, a chlorine atom, a bromine atom and a cyano group. The alkyl group, the alkoxy group, the fluoroalkyl group and the fluoroalkoxy group may be straight or branched.

From the viewpoint of availability of the material, the above $X_3$ is preferably a $C_{1-22}$ alkyl group, a $C_{1-22}$ alkoxy group, a $C_{1-12}$ fluoroalkyl group, a $C_{1-12}$ fluoroalkoxy group, a fluorine atom, a chlorine atom, a bromine atom or a cyano group. Further, in the application to a liquid crystal alignment film, from the viewpoint of the effect of increasing the pretilt angle and the stability of the pretilt angle, $X_3$ is preferably a $C_{5-22}$ alkyl group, a $C_{5-22}$ alkoxy group, a $C_{5-12}$ fluoroalkyl group or a $C_{5-12}$ fluoroalkoxy group, and is more preferably a $C_{5-12}$ alkyl group, a $C_{5-12}$ alkoxy group, a $C_{5-8}$ fluoroalkyl group or a $C_{5-8}$ fluoroalkoxy group. As the number of carbon atoms becomes large, the effects of increasing the water repellency of the polyimide precursor and the polyimide become high. In the application to the liquid crystal alignment film, as the number of carbon atoms of $X_3$ becomes large, the effect of increasing the pretilt angle of the liquid crystal becomes high. However, if the number of carbon atoms is too large, the stability of the pretilt angle tends to be reduced.

From the viewpoint as stated above, among the diaminobenzene derivatives of the present invention, preferred embodiments are shown as follows.

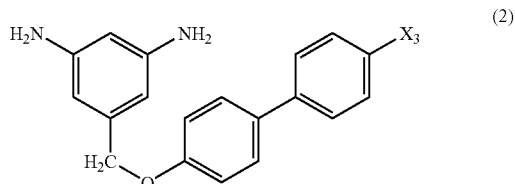

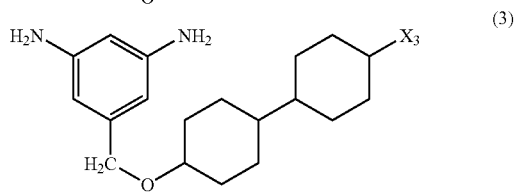

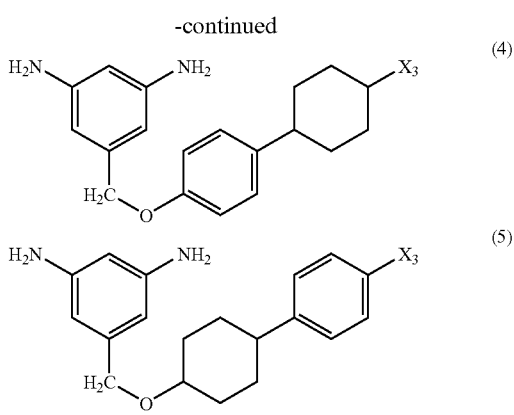

In the above structures (2) to (5), $X_3$ is an organic group selected from a $C_{5-12}$ alkyl group, a $C_{5-12}$ alkoxy group, a $C_{5-8}$ fluoroalkyl group and a $C_{5-8}$ fluoroalkoxy group.

Synthesis of the Diaminobenzene Derivative

The method for synthesis of the diaminobenzene derivative represented by the formula (1) of the present invention is not particularly limited. For example, it can be synthesized by the following method.

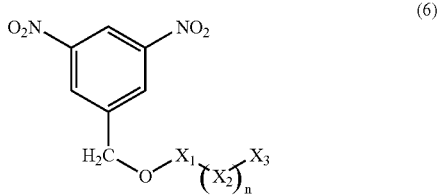

The diamine compound represented by the formula (1) of the present invention can be obtained by synthesizing the corresponding dinitro compound represented by the formula (6), followed by reducing the nitro groups to convert them into amino groups. The method of reducing the dinitro compound is not particularly limited, and is usually carried out by a reaction using e.g. hydrogen gas, hydrazine or hydrogen chloride in a solvent such as ethyl acetate, toluene, tetrahydrofuran, dioxane or an alcohol by using, as a catalyst, palladium-carbon, platinum oxide, Raney Nickel, platinum black, rhodium-alumina, platinum sulfide-carbon or the like.

The dinitro compound represented by the formula (6) can be synthesized by bonding a substituent $X_3$ to substituents $X_1$ and $X_2$ and then bonding the dinitro portion thereto via a methylene ether group (—CH$_2$O—) as a connecting portion.

Such a connecting methylene ether group (—CH$_2$O—) may be formed by a usual organic synthetic method. Specifically, it is common that the corresponding dinitro group-containing benzyl halogen derivative is reacted with a hydroxyl group-substituted derivative of the substituents $X_1$ and $X_2$ containing the substituent $X_3$, in the presence of an alkali, or the corresponding dinitro group-containing benzyl alcohol derivative is reacted with a halogen-substituted derivative of the substituents $X_1$ and $X_2$ containing the substituent $X_3$, in the presence of an alkali.

As the above-mentioned dinitro group-containing benzyl halogen derivative or the dinitro group-containing benzyl alcohol derivative, 3,5-dinitrobenzyl chloride, 3,5-dinitrobenzyl bromide and 3,5-dinitrobenzyl alcohol may, for example, be mentioned. A combination of these may suitably be selected depending upon the particular purpose in view of the availability of the material or the reaction. It should be mentioned that the compounds mentioned here are merely exemplary.

The bond between $X_1$ and $X_2$ is a single bond, various methods are available for forming such a single bond, and common organic synthetic methods such as a Grignard reaction, a Friedel-Crafts acylation method of an aromatic ring and the like, may be employed to suitably carry out the connection.

The methods for bonding $X_3$ to $X_2$ are not particularly limited. In a case where $X_3$ is an alkyl group or a fluoroalkyl group, common organic synthetic methods such as a Grignard reaction, a Friedel-Crafts acylation method of an aromatic ring, Kisner reduction method and the like may be employed. In a case where $X_3$ is an alkoxy group or a fluoroalkoxy group, it is common that the halogen derivative of $X_2$ is reacted with the hydroxyl-substituted derivative of $X_3$ in the presence of an alkali, or the hydroxyl group-substituted derivative of $X_2$ is reacted with the halogen derivative of $X_3$ in the presence of an alkali.

Polyimide Precursor and Polyimide

The polyimide precursor or the polyimide of the present invention is a polyimide precursor or a polyimide (hereinafter referred to as a specific polymer) synthesized by using the diaminobenzene derivative represented by the formula (1), as a part of the material. Such a specific polymer can be used as a resin material for coating films having the surface properties such as water repellency, and it is useful especially when it is used as a resin for a liquid crystal alignment film for a liquid crystal display device, which requires a high pretilt angle.

The method of synthesis of the specific polymer of the present invention is not particularly limited, and a method of reacting a diamine component with a tetracarboxylic acid or a tetracarboxylic acid derivative such as a tetracarboxylic acid dihalide or a tetracarboxylic dianhydride, in the same manner as in a common method for synthesis of a polyimide precursor or a polyimide. The specific polymer of the present invention can be synthesized by using the diaminobenzene derivative represented by the formula (1) as such a diamine component.

The tetracarboxylic acid and its derivative to be used to obtain the specific polymer of the present invention, are not particularly limited. Their specific examples include aromatic tetracarboxylic acids such as pyromellitic acid, 2,3,6,7-naphthalene tetracarboxylic acid, 1,2,5,6-naphthalene tetracarboxylic acid, 1,4,5,8-naphthalene tetracarboxylic acid, 2,3,6,7-anthracene tetracarboxylic acid, 1,2,5,6-anthracene tetracarboxylic acid, 3,3',4,4'-biphenyl tetracarboxylic acid, 2,3,3',4-biphenyl tetracarboxylic acid, bis(3,4-dicarboxyphenyl)ether, 3,3',4,4'-benzophenone tetracarboxylic acid, bis(3,4-dicarboxyphenyl)sulfone, bis(3,4-dicarboxyphenyl)methane, 2,2-bis(3,4-dicarboxyphenyl)propane, 1,1,1,3,3,3-hexafluoro-2,2-bis(3,4-dicarboxyphenyl)propane, bis(3,4-dicarboxyphenyl)dimethylsilane, bis(3,4-dicarboxyphenyl)diphenylsilane, 2,3,4,5-pyridine tetracarboxylic acid and 2,6-bis(3,4-dicarboxyphenyl)pyridine, and their dianhydrides and their dicarboxylic diacid halides; alicyclic tetracarboxylic acids such as 1,2,3,4-cyclobutane tetracarboxylic acid, 1,2,3,4-cyclopentane tetracarboxylic acid, 1,2,4,5-cyclohexane tetracarboxylic acid, 2,3,5-tricarboxy cyclopentylacetic acid, 3,4-dicarboxy-1,2,3,4-tetrahydro-1-naphthalene succinic acid, and their dianhydrides and their dicarboxylic diacid halides; and aliphatic tetracarboxylic acids such as 1,2,3,4-butane tetracarboxylic acid, and their dianhydrides or their dicarboxylic diacid halides.

For the application to a liquid crystal alignment film, alicyclic tetracarboxylic acids or their dianhydrides, or their dicarboxylic diacid halides are preferred from the viewpoint of the transparency of the coating film. Particularly preferred are 1,2,3,4-cyclobutane tetracarboxylic dianhydride, 3,4-dicarboxy-1,2,3,4-tetrahydro-1-naphthalene succinic dianhydride, bicyclo[3,3,0]-octane-tetracarboxylic acid and 3,5, 6-tricarboxynorbornane-2:3,5:6 dianhydride. Further, these tetracarboxylic acids and their derivatives may be used alone or in combination as a mixture of two or more of them.

For the specific polymer of the present invention, the diamine component may be a copolymer of the diaminobenzene derivative represented by the formula (1) (hereinafter referred to as the diamine (1)) with a common diamine other than that (hereinafter referred to simply as a common diamine).

The common diamine to be used in such a case, is usually a primary diamine to be used for the synthesis of a polyimide precursor or a polyimide and is not particularly limited. Its specific examples include aromatic diamines such as p-phenylenediamine, m-phenylenediamine, 2,5-diaminotoluene, 2,6-diaminotoluene, 4,4'-diaminobiphenyl, 3,3'-dimethyl-4, 4'-diaminobiphenyl, 3,3'-dimethoxy-4,4'-diaminobiphenyl, diaminodiphenyl methane, diaminodiphenyl ether, 2,2'-diaminodiphenyl propane, bis(3,5-diethyl-4-aminophenyl) methane, diaminodiphenyl sulfone, diaminobenzophenone, diaminonaphthalene, 1,4-bis(4-aminophenoxy)benzene, 1,4-bis(4-aminophenyl)benzene, 9,10-bis(4-aminophenyl) anthracene, 1,3-bis(4-aminophenoxy)benzene, 4,4'-bis(4-aminophenoxy)diphenylsulfone, 2,2-bis[4-(4-aminophenoxy)phenyl]propane, 2,2-bis[4-(4-aminophenoxy)phenyl] hexafluoropropane, alicyclic diamines such as bis(4-aminocyclohexyl)methane and bis(4-amino-3-methylcyclohexyl)methane, and aliphatic diamines such as tetramethylenediamine and hexamethylenediamine, as well as diaminosiloxane shown by:

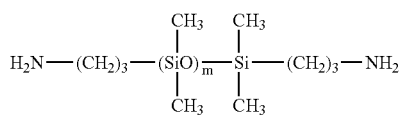

wherein m is an integer of from 1 to 10. Further, these diamines may be used alone or in combination as a mixture of two or more of them.

The proportion of the mols of the diamine (1) based on the total mols of the diamines to be used, can be optionally adjusted at the time of synthesis of the specific polymer of the present invention, and it is possible to modify the surface properties (such as water repellency) of the specific polymers obtained, in accordance with the proportion of the amount of the diamine (1). Especially, in a case where the specific polymer is used as a liquid crystal alignment film, it is possible to change the wettability with liquid crystal and further to increase the pretilt angle of liquid crystal. The proportion of the mols of the diamine (1) based on the total mols of diamines to be used in such a case, is at least 1 mol %. If it is less than 1 mol %, the effect of modifying the surface properties can not be expected so much.

Further, when it is used as a liquid crystal alignment film, the larger the proportion of the amount of the diamine (1), the higher the pretilt angle of the liquid crystal, and therefore, the proportion of the amount of the diamine (1) may be adjusted in accordance with the pretilt angle as required. The effect of increasing the pretilt angle varies depending upon the side chain structures, and the proportion of the amount of the diamine (1) may not generally be defined but is preferably within a range of from 1 mol % to 49 mol % if the required pretilt angle is from about a few degrees to ten degrees. Further, the proportion of the amount of the diamine (1) is preferably from 25 mol % to 100 mol % if the vertical alignment is required.

A known synthetic method can be used to obtain the specific polymer of the present invention by the reaction of the tetracarboxylic acid or its derivative with the diamine component. A common synthetic method may be a method of obtaining a polyamic acid as a polyimide precursor by reacting a tetracarboxylic dianhydride as a derivative of a tetracarboxylic acid, with a diamine component in an organic solvent, and a method of obtaining a polyimide by dehydration ring closure of such a polyamic acid. The reaction of the tetracarboxylic dianhydride with the diamine proceeds relatively easily in the organic solvent and is advantageous in that no byproduct will be produced. Further, the polyamic acid obtained has an advantage in environmental safety because when the polyamic acid is converted into the polyimide the by-product thereby produced will be water. Accordingly, the polyimide precursor of the present invention is also preferably a polyamic acid.

The organic solvent to be used in the reaction of the tetracarboxylic dianhydride with the diamine component is not particularly limited so long as it dissolves the polyamic acid produced. Specific examples include N,N-dimethylformamide, N,N-dimethylacetamide, N-methyl-2-pyrrolidone, N-methylcaprolactam, dimethyl sulfoxide, tetramethylurea, pyridine, dimethyl sulfone, hexamethyl sulfoxide and γ-butyrolactone. They may be used alone or in combination. Further, even a solvent which is incapable of dissolving a polyamic acid, may be used in combination with the above solvent within a range where the polyamic acid produced will not be precipitated. Further, water in the organic solvent will hinder the polymerization reaction and further causes hydrolysis of the polyamic acid produced. Therefore, the organic solvent is preferably used after being dehydrated and dried.

As a method of reacting the tetracarboxylic dianhydride with the diamine component in the organic solvent, a method of stirring a solution having the diamine component dispersed or dissolved in the organic solvent, and adding the tetracarboxylic dianhydride as it is or after dispersing or dissolving it in the organic solvent thereto, a method of adding the diamine component to a solution having the tetracarboxylic dianhydride dispersed or dissolved in the organic solvent, or a method of adding the tetracarboxylic dianhydride and the diamine component alternately to the organic solvent, may, for example, be mentioned, and any one of such methods may be employed. In a case where the tetracarboxylic dianhydride or the diamine component is composed of a plurality of compounds, they may be reacted in a preliminarily mixed state, or they may be reacted independently and sequentially, or independently reacted low molecular weight products may be mixed and reacted to obtain a polymer having a high molecular weight.

As the temperature for the above synthesis of the polyamic acid, an optional temperature of from −20 to 150° C. may be selected, but preferred is from −5 to 100° C. Further, the reaction may be carried out at an optional concentration. However, if the concentration is too low, it will be difficult to obtain a polymer having a high lo molecular weight on the other hand, if the concentration is too high, it will be difficult to stir a reaction solution uniformly because the viscosity of the reaction solution will be high. Accordingly, the concentration is preferably from 1 to 50 wt %, more preferably from 5 to 30 wt %. The reaction may be carried out at a high concentration in the initial stage, and thereafter, the organic solvent may be added to the reactor.

In the synthetic reaction of the polyamic acid, the ratio of the mols of the diamine component (the total mols of the diamine (1) and the common diamine) to the mols of the tetracarboxylic dianhydride is preferably from 0.8 to 1.2. Like in a usual polycondensation reaction, as this molar ratio becomes close to 1.0, the molecular weight of the polyamic acid produced increases.

In the present invention, if the molecular weight of the specific polymer is too small, the strength of the coating film obtainable therefrom tends to be inadequate, and if the molecular weight of the specific polymer is too large, the operation efficiency at the time of formation of the coating film and the uniformity of the coating film is likely to deteriorate. Accordingly, the molecular weight of the specific polymer in the present invention is preferably adjusted to be from 10,000 to 1,000,000 by the weight-average molecular weight as measured by GPC (Gel Permeation Chromatography) method.

As a method for obtaining a polyimide by dehydration ring closure of a polyamic acid, it is common to employ thermal imidation of the solution of the polyamic acid or catalytic imidation by adding a catalyst to the solution of the polyamic acid. Among them, the catalytic imidation in which the imidation reaction proceeds at a relatively low temperature, is preferred, since the molecular weight of the obtainable polyimide does not tend to decrease.

The thermal imidation of the polyamic acid is carried out in the solution at a temperature of from 100 to 400° C., preferably from 120 to 250° C., and the thermal imidation is preferably carried out while removing water produced by the dehydration ring closure reaction out of the system.

The catalytic imidation of the polyamic acid may be carried out by adding a basic catalyst such as pyridine, triethylamine, trimethylamine, tributylamine or triocrylamine and an acid anhydride such as acetic anhydride, trimellitic anhydride or pyromellitic anhydride to the solution of the polyamic acid, followed by stirring at a temperature of from −20 to 250° C., preferably from 0 to 180° C. The amount of the basic catalyst is from 0.5 to 30 times by mol, preferably from 2 to 20 times by mol based on the amic acid groups, and the amount of the acid anhydride is from 1 to 50 times by mol, preferably from 3 to 30 times by mol based on the amic acid groups. If the amount of the basic catalyst or the acid anhydride is small, the reaction tends to be inadequate, and if it is too large, the complete removal of the basic catalyst or the acid anhydride tends to be difficult after completion of the reaction. Among such basic catalysts, pyridine is preferred because of basicity at a proper level for proceeding the reaction. Further, among such acid anhydrides, acetic anhydride is preferred because purification after completion of the reaction is easy. The imidation ratio due to the catalytic imidation can be controlled by adjusting the amount of the catalyst, the reaction temperature and the reaction time.

In order to recover the specific polymer from the reaction solution of the specific polymer of the present invention, the reaction solution may be put into a poor solvent to precipitate the specific polymer. The poor solvent to be used for precipitation and recovery of the specific polymer is not particularly limited, and methanol, acetone, hexane, butyl cellosolve, heptane, methyl ethyl ketone, methyl isobutyl ketone, ethanol, toluene or benzene may, for example, be mentioned. The specific polymer precipitated in the poor solvent, is recovered by filtration and then, dried at room temperature or under heating, under atmospheric pressure or reduced pressure, to obtain a powder. Further, impurities in the specific polymer can be reduced by repeating for from 2 to 10 times an operation of redissolving the specific polymer precipitated and recovered in the organic solvent, followed by re-precipitation and recovery. In such a case, it is preferred to use, as poor solvents, at least three types of poor solvents such as alcohols, ketones and hydrocarbons, since purification efficiency will thereby be further increased.

Treating Agent for Liquid Crystal Alignment

The treating agent for liquid crystal alignment of the present invention is a composition for forming a liquid crystal alignment film, and is characterized in that it contains at least one specific polymer (namely, the polyimide precursor or the polyimide synthesized by using the diaminobenzene derivative represented by the formula (1) as a part of the material) as mentioned above. Further, its form is not particularly limited, but is preferably a coating solution obtained by dissolving the specific polymer in an organic solvent because it is necessary to form a uniform thin film having a thickness of from 0.01 to 1.0 μm on a substrate when it is to be used as a liquid crystal alignment film.

In order to obtain the coating solution as the treating agent for liquid crystal alignment of the present invention, a method of diluting the reaction solution of the specific polymer with the organic solvent or a method of dissolving the specific polymer precipitated and recovered in the organic solvent may, for example, be mentioned. The solid content concentration of the coating solution can suitably be changed depending upon the thickness of the liquid crystal alignment film to be obtained and is preferably from 1 to 10 wt %. If the solid content concentration is less than 1 wt %, it tends to be difficult to form a uniform coating film with no defect, and if it is more than 10 wt %, it tends to be difficult to form a thin film having a thickness of at most 1 μm.

With respect to the treating agent for the liquid crystal alignment of the present invention, the reaction solution of the specific polymer may be used as it is or after precipitated and recovered. However, in the case of the polyimide solution which is subjected to the catalytic imidation, it is preferably used after precipitated and recovered because the basic catalyst or acid anhydride remaining in the solution tends to present an adverse effect on the liquid crystal display device.

The organic solvent which dissolves the specific polymer is not particularly limited so long as it is capable of dissolving the specific polymer. For example, N,N-dimethylformamide, N,N-dimethylacetamide, N-methyl-2-pyrrolidone, N-methylcaprolactam, 2-pyrrolidone, N-ethyl pyrrolidone, N-vinyl pyrrolidone, dimethyl sulfoxide, tetramethylurea, pyridine, dimethyl sulfone, hexamethyl sulfoxide and y-butyrolactone may be mentioned. These solvents may be used alone or in combination as a mixture. Further, these organic solvents may be used for diluting the coating solution.

The treating agent for liquid crystal alignment of the present invention may optionally preferably contain a solvent or a compound which improves uniformity in the film thickness at the time of forming a coating film, a compound which improves the adhesion between the coating film and the substrate, and the like, in addition to the specific polymer and the solvent which dissolves the specific polymer. These components may be added to the solution of the specific polymer, which is preliminarily prepared.

The following may be mentioned as specific examples of the solvent which improves the uniformity of the film thickness at the time of forming a coating film. A solvent having a surface tension such as ethyl cellosolve, butyl cellosolve, ethyl carbitol, butyl carbitol, ethyl carbitol acetate, ethylene glycol, 1-methoxy-2-propanol, 1-ethoxy-2-propanol, 1-butoxy-2-propanol, 1-phenoxy-2-propanol, propylene glycol monoacetate, propylene glycol diacetate, propylene glycol-1-monomethyl ether-2-acetate, propylene glycol-1-monoethyl ether-2-acetate, dipropylene glycol, 2-(2-ethoxypropoxy)propanol, methyl lactate, ethyl lactate, n-propyl lactate, n-butyl lactate or isoamyl lactate. These solvents may be used alone or in combination as a mixture of two or more of them. When such a solvent is incorporated, its total amount is preferably from 5 to 80 wt %, more preferably from 20 to 60 wt % in the total solvents. If it is less than 5 wt %, such an effect can not be expected very much. On the other hand, if it is more than 80 wt %, the specific polymer tends to be precipitated, since such a solvent usually has low ability to dissolve the specific polymer.

The following may be mentioned as specific examples of the compound which improves the adhesion to the coating film and the substrate. A functional silane-containing compound or an epoxy group-containing compound such as 3-aminopropyltrimethoxysilane, 3-aminopropyltriethoxysilane, 2-aminopropyltrimethoxysilane, 2-aminopropyltriethoxysilane, N-(2-aminoethyl)-3-aminopropyltrimethoxysilane, N-(2-aminoethyl)-3-aminopropylmethyldimethoxysilane, 3-ureidepropyltrimethoxysilane, 3-ureidepropyltriethoxysilane, N-ethoxycarbonyl-3-aminopropyltrimethoxysilane, N-ethoxycarbonyl-3-aminopropyltriethoxysilane, N-triethoxysilylpropyltriethylenetriamine, N-trimethoxysilylpropyltriethylenetriamine, 10-trimethoxysilyl-1,4,7-triazadecane, 10-triethoxysilyl-1,4,7-triazadecane, 9-trimethoxysilyl-3,6-diazanonyl acetate, 9-triethoxysilyl-3,6-diazanonyl acetate, N-benzyl-3-aminopropyltrimethoxysilane, N-benzyl-3-aminopropyltriethoxysilane, N-phenyl-3-aminopropyltrimethoxysilane, N-phenyl-3-aminopropyltriethoxysilane, N-bis(oxyethylene)-3-aminopropyltrimethoxysilane, N-bis(oxyethylene)-3-aminopropyltriethoxysilane, ethylene glycol diglycidyl ether, polyethylene glycol diglycidyl ether, propylene glycol diglycidyl ether, tripropylene glycol diglycidyl ether, polypropylene glycol diglycidyl ether, neopentyl glycol diglycidyl ether, 1,6-hexanediol diglycidyl ether, glycerin diglycidyl ether, 2,2-dibromoneopentyl glycol diglycidyl ether, 1,3,5,6-tetraglycidyl-2,4-hexanediol, N,N,N',N'-tetraglycidyl-m-xylenediamine, 1,3-bis(N,N-diglycidyl aminomethyl)cyclohexane or N,N,N',N'-tetraglycidyl-4,4'-diaminodiphenylmethane. When such a compound is incorporated, it is preferably from 0.1 to 30 wt %, more preferably from 1 to 20 wt % based on the total polymer weight. If it is less than 0.1 wt %, the effect of improving the adhesion can not be expected, and if it is more than 30 wt %, the alignment property of the liquid crystal tends to deteriorate.

The treating agent for liquid crystal alignment of the present invention may contain polymer components or compounds other than the specific polymer within a range not to impair the effect of the present invention. Further, for the purpose of changing electrical properties such as the dielectric constant and electroconductivity of the liquid crystal alignment film, a dielectric or electroconductive substance may be added thereto.

The treating agent for liquid crystal alignment of the present invention can be applied on a substrate and fired, followed by treatment for alignment by rubbing or light irradiation, or followed by no treatment for alignment in the application for a vertical alignment, and used as a liquid crystal alignment film. It is useful especially for an application wherein rubbing is carried out to form the liquid crystal alignment film.

The method of applying the treating agent for liquid crystal alignment of the present invention is not particularly limited. In the case of a liquid crystal alignment film, the film thickness, the dimensional precision of the coating film and the uniformity of the surface will be particularly important, and therefore, it is industrially common to apply it by a printing machine for e.g. screen printing, offset printing or inkjet printing, by using a coating solution of the treating agent for liquid crystal alignment. In addition, as a method of using the coating solution, a dip coater, a roll coater, a spinner or the like may be employed depending upon the particular purpose. After coating the substrate with the solution by such a method, the solvent is evaporated at a temperature of from 50 to 150° C., preferably from 80 to 120° C., by a heating means such as a hotplate to form a coating film.

In a case where the specific polymer contained in the treating agent for liquid crystal alignment of the present invention is a polyimide precursor, a polyimide coating film can be obtained by forming a coating film on the substrate, followed by firing. This firing can be carried out at an optional temperature of from 100 to 350° C., but it is preferably from 150 to 300° C., more preferably from 200 to 250° C. The higher the firing temperature, the higher the conversion to a polyimide. However, when used as a liquid crystal alignment film, the polyimide may not necessarily be a complete polyimide and may be a mixture of a polyimide precursor and a polyimide. However, it is preferably fired at a temperature higher by at least 10° C. than the heat treatment temperature which is required in the subsequent process for production a liquid crystal cell. Further, in a case where the specific polymer contained in the treating agent for liquid crystal alignment of the present invention is a polyimide, the firing process is not necessarily required. However, it is preferred to carry out the firing at a temperature higher by at least 10° C. than the heat treatment temperature which is required in the subsequent process for production of a liquid crystal cell.

The liquid crystal alignment film obtained from the treating agent for liquid crystal alignment of the present invention can be formed into a liquid crystal display device by preparing a liquid crystal cell by a well-known method. As an example of the preparation of the liquid crystal cell, it is common to employ a method wherein a pair of substrates having liquid crystal alignment films formed, are set with a spacer of from 1 to 30 µm, preferably from 2 to 10 µm, interposed, so that the alignment treatment direction has an optional angle of from 0 to 270°, the periphery is fixed with a sealing agent, and liquid crystal is injected and sealed-in. A method for sealing-in the liquid crystal is not particularly limited, and a vacuum method of reducing the pressure in the liquid crystal cell prepared, and then injecting liquid crystal, or a dropping method of dropping liquid crystal, followed by sealing, may, for example, be mentioned.

The liquid crystal display device thus prepared by using the treating agent for liquid crystal alignment of the present invention gives a high and stable pretilt angle of liquid crystal and is suitably used as a liquid crystal display device which requires a high pretilt angle.

Now, the present invention will be described in further detail with reference to Examples, but the present invention is by no means restricted thereto.

EXAMPLES

Example 1

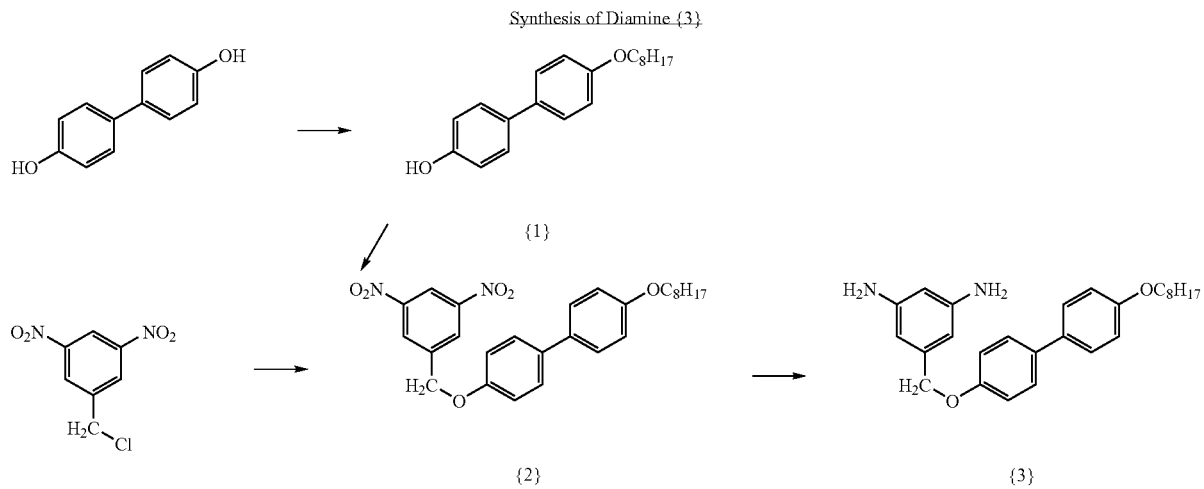

Synthesis of Diamine {3}

Into a 1,000 ml four neck flask, biphenol (100.00 g, 0.538 mol), 1-bromooctane (103.90 g, 0.538 mol), potassium carbonate (111.54 g, 0.807 mol) and N,N'-dimethylacetamide (DMAc) (400 ml) were put and stirred for 10 hours at a reaction temperature of 110° C. After completion of the reaction, the potassium carbonate was filtered off. The filtrate was distilled under reduced pressure, a 1N-sodium hydroxide (NaOH) solution was added to the residue, and the precipitated solid was collected by filtration. The obtained solid was recrystallized from methanol to obtain colorless crystals {1} (76.55 g, 48%, mp: 149 to 154° C.).

1H-NMR (CDCl3, δppm): 7.41-7.46 (4H, m), 6.94 (2H, d), 6.88 (2H, d), 4.73 (1H, s), 3.98 (2H, t), 1.80 (2H, m), 1.47 (2H, m), 1.30 (8H, m), 0.89 (3H, t).

Into a 300 ml four neck flask, 3,5-dinitrobenzyl chloride (13.04 g, 60.21 mmol), {1} (18.08 g, 60.56 mmol) and tetrahydrofuran (THF) (200 ml) were put and stirred at room temperature until the solution became uniform. Then, an aqueous NaOH solution (NaOH (0.27 g)/H₂O (50 ml)) was dropwise slowly added thereto. After completion of the dropwise addition, refluxing was gently carried out for 13 hours. The reaction solution was distilled under reduced pressure, water was added to the residue, and a solid was collected by filtration. The solid obtained was washed with methanol and recrystallized from ethanol to obtain yellow crystals {2} (21.55 g, 75%, mp: 111 to 112° C.).

1H-NMR (CDCl3, δppm): 9.01 (1H, S), 8.67 (2H, S), 7.51 (2H, d), 7.46 (2H, d), 7.04 (2H, d), 6.95 (2H, d), 5.28 (2H, S), 3.99 (2H, t), 1.80 (2H, m), 1.47 (2H, m), 1.32 (8H, m), 0.89 (3H, t).

Into a 500 ml four neck flask, {2} (10.00 g, 20.90 mmol) and dioxane (300 ml) were put, and the reactor was flushed with nitrogen. Then, platinum (IV) oxide (PtO₂) (1.00 g) was put. The interior of the reactor was made to be a hydrogen atmosphere, and stirring was carried out at 60° C. for 7 hours and at room temperature for 14 hours. After completion of the reaction, PtO₂ was filtered off, and the filtrate was distilled under reduced pressure. The residue was washed with methanol to obtain diamine {3} as slightly fresh color crystals {3} (6.33 g, 72%, mp: 192 to 196° C.).

1H-NMR (CDCl3, δppm): 7.45 (4H, m), 7.00 (2H, d), 6.94 (2H, d), 4.92 (2H, s), 3.98 (2H, t), 3.61 (4H, s), 1.80 (2H, m), 1.47 (2H, m), 1.32 (8H, m), 0.89 (3H, t).

Example 2

Synthesis of Diamine {5}

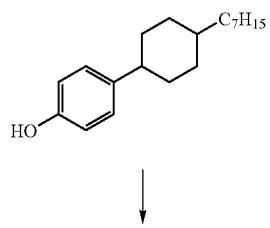

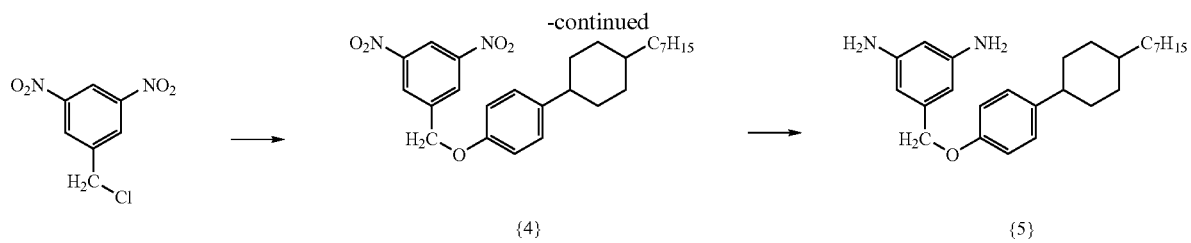

Into a 1,000 ml four neck flask, phenylcyclohexyl derivative (50.00 g, 0.182 mol) and THF (300 ml) were put and stirred until they became uniform. The reaction solution was left to stand at room temperature, and 3,5-dinitrobenzyl chloride (41.39 g, 0.191 mol) was added thereto. Then, a NaOH solution (NaOH (29.12 g)/$H_2O$ (200 ml)) was dropwise slowly added thereto. After completion of the dropwise addition, refluxing was carried out for 8 hours. After completion of the reaction, the reaction solution was distilled under reduced pressure. The filtration was carried out, and a filter cake was washed with water, methanol and acetonitrile. Thereafter, it was recrystallized from acetonitrile to obtain yellow crystals {4} (54.32 g, 66%, mp: 113 to 114° C.).

1H-NMR (d-DMSO, δppm): 8.99 (1H, s), 8.65 (2H, d), 7.17 (2H, d), 6.91 (2H, d), 5.23 (2H, s), 2.43 (1H, t), 1.21 to 1.43 (16H, m), 1.06 (2H, m), 0.89 (3H, t).

Into a 1,000 ml four neck flask, {4} 40.00 g, 88.00 mmol) and dioxane (500 ml) were put, and the reactor was flushed with nitrogen, and then $PtO_2$ (4.00 g) was put. The interior of the reactor was made to be a hydrogen atmosphere, and stirring was carried out at room temperature for 24 hours. After completion of the reaction, $PtO_2$ was filtered off, and the filtrate was distilled under reduced pressure. Methanol was added to the residue, and a slightly yellow solid was precipitated. Filtration was carried out to obtain diamine {5} as a slightly yellow solid (26.55 g, 76%, mp: 153 to 157° C.).

1H-NMR (CDCl3, δppm): 7.09 (2H, d), 6.88 (2H, d), 5.84 (2H, s), 5.74 (1H, s), 4.74 (4H, s), 3.33 (2H, S), 2.36 (1H, t), 1.77 (4H, m), 1.17 to 1.41 (16H, m), 1.01 (2H, m), 0.88 (3H, t).

Example 3

Synthesis of Polyimide Precursor [A]

Using the diamine {3} (1.64 g, 5.21 mmol) obtained in Example 1, 1,4-diamiminobenzene (2.25 g, 20.81 mmol), 3,4-dicarboxy-1,2,3,4-tetrahydro-1-naphthalene succinic dianhydride (7.81 g, 26.01 mmol) and N-methyl-2-pyrrolidone (NMP) (46.80 g), a polycondensation reaction was carried out by stirring at room temperature to obtain a polyimide precursor solution [A] having a solid content concentration of 20 wt %. The viscosity of this solution was 3,481 mPa·s (25° C.: by E model viscometer), and the weight average molecular weight as measured by GPC (Gel Permeation chromatography) was 134,600.

Example 4

Synthesis of Polyimide Precursor [B]

Using the diamine {5} (3.39 g, 8.59 mmol) obtained in Example 2, 1,4-diaminobenzene (3.72 g, 34.41 mmol), 3,4-dicarboxy-1,2,3,4-tetrahydro-1-naphthalene succinic dianhydride (12.91 g, 42.99 mmol) and NMP (80.08 g), a polycondensation reaction was carried out by stirring at room temperature to obtain a polyimide precursor solution [B] having a solid content concentration of 20 wt %. The viscosity of this solution was 3,532 mPa·s (25° C.: by E model viscometer), and the weight average molecular weight as measured by GPC method was 145,000.

Example 5

Synthesis of Polyimide Precursor [C]

Using the diamine {5} (1.70 g, 4.30 mmol) obtained in Example 2, 1,4-diaminobenzene (4.18 g, 38.70 mmol), 3,4-dicarboxy-1,2,3,4-tetrahydro-1-naphthalene succinic dianhydride (12.91 g, 42.99 mmol) and NMP (80.08 g), a polycondensation reaction was carried out by stirring at room temperature to obtain a polyimide precursor solution [C] having a solid content concentration of 20 wt %. The viscosity of this solution was 4,120 mPa·s (25° C.: by E model viscometer), and the weight average molecular weight as measured by GPC was 185,000.

Examples 6, 7 and 8

Production of Treating Agents for Liquid Crystal Alignment

Each of the polyimide precursor solutions ([A], [B] and [C]) obtained in Examples 3, 4 and 5 was diluted with NMP and butyl cellosolve to obtain a treating agent for liquid crystal alignment having a resin concentration of 5 wt %, butyl cellosolve of 20 wt % and NMP of 75 wt %.

Preparation of Liquid Crystal Cell

The above treating agent for liquid crystal alignment was spin-coated on an ITO surface of a glass substrate having an ITO electrode and subjected to heat treatment at 80° C. for 5 minutes and at 220° C. for one hour to form a polyimide coating film having a film thickness of 0.1 μm. The coating film surface was subjected to rubbing treatment under the conditions of a rotational speed of 300 rpm, a rotational speed of 20 mm/sec and a processing amount of 0.3 mm, by a rubbing means provided with a rayon cloth.

Thereafter, using a pair of such substrates as one set, a spacer of 6 μm was applied, and these substrates were laminated so that the film surfaces were located inside and the rubbing directions crossed each other. Then, nematic liquid crystal (MLC-2003, manufactured by Merck Company) was injected to prepare a 90 degree twisted liquid crystal cell. The alignment state of this liquid crystal cell was observed and confirmed to be uniform alignment without any defect.

Measurement of Pretilt Angle

Immediately after cell preparation (25° C.), these cells were heat-treated at 95° C. for 5 minutes, and further heat-treated at 120° C. for one hour. Then, the pretilt angles were measured by a crystal rotation method. Further, measurements of pretilt angles immediately after cell preparation (25° C.) were carried out also when the rubbing pressing amounts were respectively 0.3 mm, 0.5 mm and 0.7 mm.

The results are shown in Tables 1 and 2 given hereinafter.

Comparative Example 1

For the purpose of comparison in evaluation of thermal stability of the pretilt angle, the following diamine {6} was used.

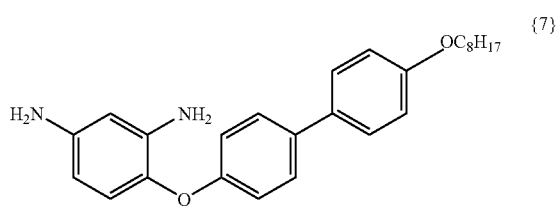

The diamine {7} was synthesized by the following path.

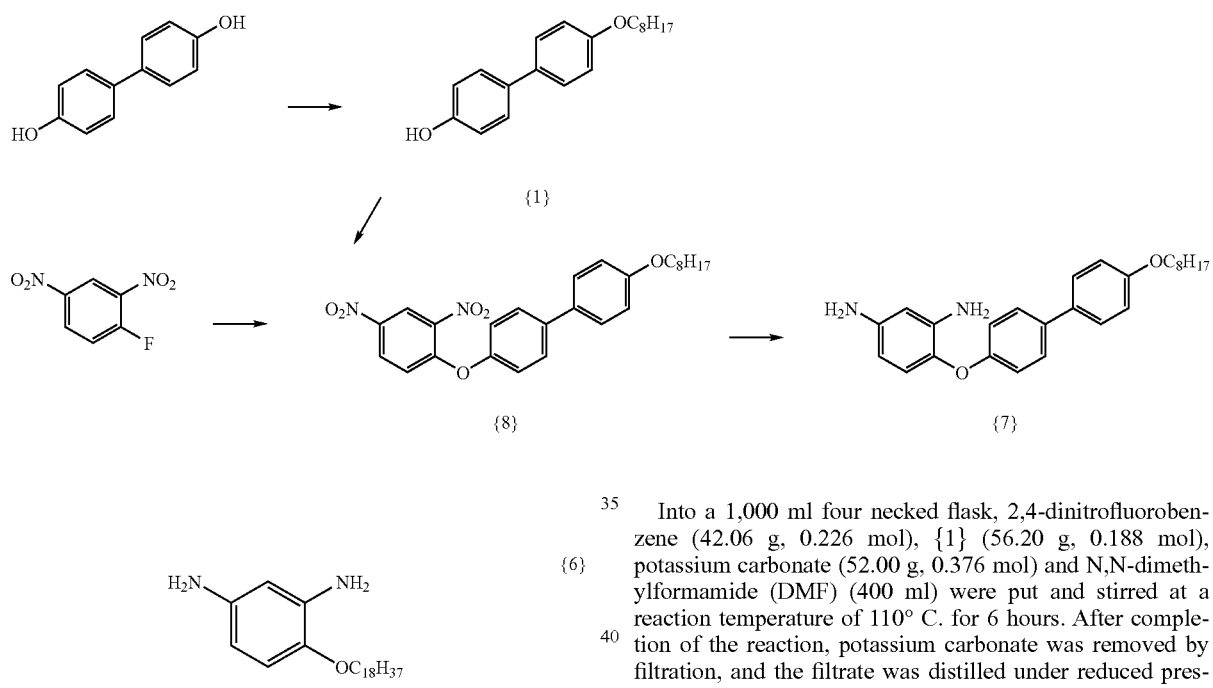

Using the diamine {6}, a synthesis of a polyimide precursor [D] was carried out.

Using the diamine {6} (9.79 g, 25.99 mmol), 1,4-diaminobenzene (11.25 g, 104.03 mmol), 3,4-dicarboxy-1,2,3,4-tetrahydro-1-naphthalene succinic dianhydride (39.04 g, 130.02 mmol) and NMP (240.32 g), a polycondensation reaction was carried out by stirring at room temperature to obtain a polyimide precursor solution [D] having a solid content concentration of 20 wt %. The viscosity of this solution was 730 mPa·s (25° C.: by E model viscometer), and the weight average molecular weight as measured by GPC was 66,000.

Using the polyimide precursor solution [D] thus obtained, treating agents for liquid crystal alignment were produced by the same methods as in Examples 6, 7 and 8, and liquid crystal cells were prepared whereupon the pretilt angles were measured. The results are shown in Table 1 given hereinafter.

Comparative Example 2

For comparison in evaluation of rubbing pressure dependence of the pretilt angle, the following diamine {7} was used.

Into a 1,000 ml four necked flask, 2,4-dinitrofluorobenzene (42.06 g, 0.226 mol), {1} (56.20 g, 0.188 mol), potassium carbonate (52.00 g, 0.376 mol) and N,N-dimethylformamide (DMF) (400 ml) were put and stirred at a reaction temperature of 110° C. for 6 hours. After completion of the reaction, potassium carbonate was removed by filtration, and the filtrate was distilled under reduced pressure. Then, methanol was added to the residue to precipitate an yellow solid. The obtained solid was recrystallized from THF to obtain slightly yellow crystals {8} (65.33 g, 75%, mp: 127 to 129° C.).

1H-NMR (CDCl3, δppm): 8.84 (1H, s), 8.31 (1H, d), 7.63 (2H, d), 7.50 (2H, d), 7.17 (2H, d), 7.10 (1H, d), 6.98 (2H, d), 4.00 (2H, t), 1.81 (2H, m), 1.48 (2H, m), 1.31 (8H, m), 0.89 (3H, t)

Into a 1,000 ml four necked flask, {8} (35.45 g, 75.35 mmol) and dioxane (400 ml) were put, the reactor was flushed with nitrogen, and then Pd—C (3.55 g) was added thereto. Then, the interior of the reactor was changed to a hydrogen atmosphere, followed by stirring at 60° C. for 50 hours and at room temperature for 120 hours. After completion of the reaction, Pd—C was removed by filtration, and the filtrate was distilled under reduced pressure. The residue was recrystallized from acetonitrile to obtain the diamine {7} (23.55 g, 77%, mp: 196 to 198° C.) as slightly reddish brown crystals.

1H-NMR (CDCl3, δppm): 7.41 to 7.45 (4H, m), 6.96 (2H, d), 6.93 (2H, d), 6.77 (1H, d), 6.18 (1H, s), 6.10 (1H, d), 3.98 (2H, t), 3.54 to 3.70 (4H, broad), 1.79 (2H, m), 1.46 (2H, m), 1.31 (8H, m), 0.89 (3H, t).

Using the diamine {7}, a synthesis of a polyimide precursor [E] was carried out.

Using the diamine {7} (2.53 g, 6.25 mmol), 1,4-diaminobenzene (2.03 g, 18.77 mmol), 3,4-dicarboxy-1,2,3,4-tetrahydro-1-naphthalene succinic dianhydride (7.51 g, 25.01 mmol) and NMP (48.28 g), a polycondensation reaction was carried out by stirring at room temperature to obtain a polyimide precursor solution [E] having a solid content concentration of 20 wt %. The viscosity of this solution was 435 mPa·s (25° C.: by E model viscometer), and the weight average molecular weight as measured by GPC method was 44,800.

Using the polyimide precursor solution [E] thus obtained, treating agents for liquid crystal alignment were produced by the same methods as in Examples 6, 7 and 8, and liquid crystal cells were prepared, whereupon the pretilt angles were measured. The results are shown in Table 2 given below.

TABLE 1

EVALUATION RESULTS
Measurement of pretilt angles ①
(evaluation of thermal stability of pretilt angles)

| Polyimide precursor solution | Diamine (Amount %) | Pretilt angle (°) Initial stage (25° C.) | Pretilt angle (°) After treatment at 120° C. for 5 minutes | Pretilt angle (°) After treatment at 120° C. for 1 hour |
|---|---|---|---|---|
| Ex. | | | | |
| 6 | A | {3} (20) | 6.8 | 6.9 | 6.9 |
| 7 | B | {5} (20) | 20 | 21 | 21 |
| Comp. Ex. | | | | |
| 1 | D | {6} (20) | 8 | 7.5 | 6.3 |

*In each cell, uniform alignment without any defect was observed.

TABLE 2

Measurement of pretilt angles ②
(evaluation of dependency of pretilt angles on rubbing pressure)

| Polyimide precursor solution | Diamine (Amount %) | Pretilt angle (°) Pressing amount 0.3 mm | Pretilt angle (°) Pressing amount 0.5 mm | Pretilt angle (°) Pressing amount 0.7 mm |
|---|---|---|---|---|
| Ex. | | | | |
| 6 | A | {3} (20) | 6.8 | 6.8 | 6.9 |
| 8 | C | {5} (10) | 6.1 | 5.9 | 5.9 |
| Comp. Ex. | | | | |
| 2 | E | {7} (25) | 6.1 | 5.8 | 6.8 |

Diamines {3} and {5} were excellent in the effects of increasing pretilt angles. Further, from the comparison with the evaluation of the thermal stability of the pretilt angle of the diamine {6}, the diamines {3} and {5} of the present invention were found to be excellent in the thermal stability of pretilt angles. In addition, from the comparison with the evaluation of the dependency of the diamine {7} on rubbing pressure, the dependency of the diamines {3} and {5} of the present invention was found to be small.

INDUSTRIAL APPLICABILITY

The diaminobenzene derivative of the present invention is easy to synthesize in the well-known reaction path and has high reactivity. Therefore, it can be used as a material for various polymers. Especially when it is used as the material for a resin of a liquid crystal alignment film, the effect of increasing the pretilt angle of liquid crystal is high, and a high and stable pretilt angle can be imparted to the liquid crystal.

The polyimide precursor or the polyimide of the present invention can be used as a resin material for a coating film having surface properties such as water repellency. Especially when it is used as a liquid crystal alignment film, a high and stable pretilt angle can be imparted to liquid crystal.

The treating agent for liquid crystal alignment of the present invention can give a liquid crystal alignment film having a high pretilt angle of liquid crystal, excellent thermal stability of the pretilt angle and low dependency of the pretilt angle on rubbing pressure.

What is claimed is:

1. A diaminobenzene derivative represented by the formula (1):

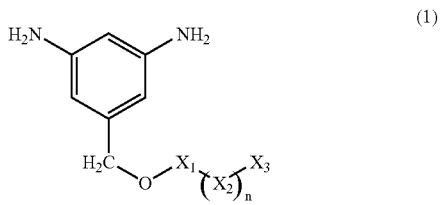

wherein $X_1$ and $X_2$ are each independently a monocyclic group selected from a benzene ring, a cyclohexane ring and a heterocyclic ring, wherein optional hydrogen atom(s) on the monocyclic group may be substituted by substituent(s) selected from the group consisting of a $C_{1-3}$ alkyl group, a $C_{1-3}$ alkoxy group, a $C_{1-3}$ fluoroalkyl group, a $C_{1-3}$ fluoroalkoxy group, and a cyano group; n is an integer of 0 or 1; when n=0, and $X_3$ is a member selected from the group consisting of a $C_{1-32}$ alkyl group, a $C_{1-32}$ alkoxy group, a $C_{1-32}$ fluoroalkyl group, a $C_{1-32}$ fluoroalkoxy group, and a cyano group, and when n=1, $X_3$ is a member selected from the group consisting of a $C_{1-32}$ alkyl group, a $C_{1-32}$ alkoxy group, a $C_{1-32}$ fluoroalkyl group, a $C_{1-32}$ fluoroalkoxy group, a fluorine atom, a chlorine atom, a bromine atom and a cyano group.

2. The diaminobenzene derivative according to claim 1, wherein in the formula (1), $X_1$ is a benzene ring or a cyclohexane ring, $X_2$ is a benzene ring or a cyclohexane ring, and n is 1.

3. The diaminobenzene derivative according to claim 1, wherein in the formula (1), $X_1$ is a benzene ring or a cyclohexane ring, $X_2$ is a benzene ring, and n is 1.

4. The diaminobenzene derivative according to claim 1, wherein in the formula (1), $X_1$ is a benzene ring or a cyclohexane ring, $X_2$ is a cyclohexane ring, and n is 1.

5. The diaminobenzene derivative according to claim 2, wherein $X_3$ is an organic group selected from the group consisting of a $C_{5-12}$ alkyl group, a $C_{5-12}$ alkoxy group, a $C_{5-8}$ fluoroalkyl group, and a $C_{5-8}$ fluoroalkoxy group.

6. A polyimide precursor or a polyimide obtained by reaction of an acid dianhydride with a diamine starting material comprising any one diaminobenzene derivative as defined in claim 1.

7. A liquid crystal alignment agent comprising at least one of the polyimide precursor and the polyimide as defined in claim 6.

8. The diaminobenzene derivative according to claim 3 wherein $X_3$ is an organic group selected from the group consisting of a $C_{5-12}$ alkyl group, a $C_{5-12}$ alkoxy group, a $C_{5-8}$ fluoroalkyl group and a $C_{5-8}$ fluoroalkoxy group.

9. The diaminobenzene derivative according to claim 4 wherein $X_3$ is an organic group selected from the group consisting of a $C_{5-12}$ alkyl group, a $C_{5-12}$ alkoxy group, a $C_{5-8}$ fluoroalkyl group and a $C_{5-8}$ fluoroalkoxy group.

10. A polyimide precursor or a polyimide obtained by reaction of an acid dianhydride with a diamine starting material comprising any one diaminobenzene derivative as claimed in claim 2.

11. A polyimide precursor or a polyimide obtained by reaction of an acid dianhydride with a diamine starting material comprising any one diaminobenzene derivative as claimed in claim 3.

12. A polyimide precursor or a polyimide obtained by reaction of an acid dianhydride with a diamine starting material comprising any one diaminobenzene derivative as claimed in claim 4.

13. A polyimide precursor or a polyimide obtained by reaction of an acid dianhydride with a diamine starting material comprising any one diaminobenzene derivative as claimed in claim 5.

14. A liquid crystal alignment agent comprising at least one of the polyimide precursor and the polyimide as claimed in claim 10.

15. A liquid crystal alignment agent comprising at least one of the polyimide precursor and the polyimide as claimed in claim 11.

16. A liquid crystal alignment agent comprising at least one of the polyimide precursor and the polyimide as claimed in claim 12.

17. A liquid crystal alignment agent comprising at least one of the polyimide precursor and the polyimide as claimed in claim 13.

18. A liquid crystal alignment film made of the liquid crystal alignment agent as claimed in claim 7.

19. A liquid crystal alignment film made of the liquid crystal alignment agent as claimed in claim 14.

20. A liquid crystal device comprising the alignment film as claimed in claim 18.

* * * * *